(12) United States Patent
Peter et al.

US011414695B2

(10) Patent No.: US 11,414,695 B2
(45) Date of Patent: Aug. 16, 2022

(54) NUCLEIC ACID ENRICHMENT USING CAS9

(71) Applicant: Agilent Technologies, Inc., Loveland, CO (US)

(72) Inventors: Brian Jon Peter, Los Altos, CA (US); Robert A. Ach, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/290,901

(22) Filed: May 29, 2014

(65) Prior Publication Data

US 2014/0356867 A1   Dec. 4, 2014

Related U.S. Application Data

(60) Provisional application No. 61/828,507, filed on May 29, 2013, provisional application No. 61/831,061, filed on Jun. 4, 2013.

(51) Int. Cl.
*C12Q 1/6806* (2018.01)
*C12N 9/22* (2006.01)
*C12N 15/10* (2006.01)
*C12Q 1/6869* (2018.01)

(52) U.S. Cl.
CPC ............ *C12Q 1/6806* (2013.01); *C12N 9/22* (2013.01); *C12N 15/1003* (2013.01); *C12N 15/1034* (2013.01); *C12Q 1/6869* (2013.01); *C12Y 301/00* (2013.01); *Y10T 436/143333* (2015.01)

(58) Field of Classification Search
None
See application file for complete search history.

(56) References Cited

U.S. PATENT DOCUMENTS

| 10,266,850 B2 | 4/2019 | Doudna et al. | |
|---|---|---|---|
| 2012/0164689 A1* | 6/2012 | Fujii | C12N 15/1086 435/91.1 |
| 2014/0038241 A1 | 2/2014 | Zhou et al. | |
| 2014/0068797 A1 | 3/2014 | Doudna et al. | |
| 2014/0127752 A1 | 5/2014 | Zhou et al. | |
| 2014/0179006 A1 | 6/2014 | Zhang | |
| 2014/0315985 A1 | 10/2014 | May et al. | |
| 2014/0357530 A1* | 12/2014 | Zhang | C12N 15/63 506/16 |
| 2015/0045546 A1* | 2/2015 | Siksnys | C12N 9/22 536/23.1 |
| 2015/0089681 A1* | 3/2015 | Van Der Oost | G01N 33/542 800/25 |
| 2016/0002670 A1 | 1/2016 | Church et al. | |

FOREIGN PATENT DOCUMENTS

| WO | WO2013141680 | 9/2013 | | |
|---|---|---|---|---|
| WO | WO2013142578 | 9/2013 | | |
| WO | WO 2013/176772 | * 11/2013 | ............ | C12N 15/11 |
| WO | WO2013176772 | 11/2013 | | |
| WO | WO2013188638 | 12/2013 | | |
| WO | WO2014018423 | 1/2014 | | |
| WO | WO 2014/125668 | * 8/2014 | ............ | C12N 15/09 |

OTHER PUBLICATIONS

Jinek et al., A Programmable Dual-RNA-Guided DNA Endonuclease in Adaptive Bacterial Immunity, Science, Aug. 17, 2012, vol. 337.*
Pandey et al., Hsp27 functions as a negative regulator of cytochrome c-dependent activation of procaspase-3, Oncogene (2000) 19, 1975-1981.*
Elshire et al., A Robust, Simple Genotyping-by-Sequencing (GBS) Approach for High Diversity Species, PLoS ONE, May 2011, vol. 6, Issue 5, e19379.*
Parameswaran et al., A pyrosequencing-tailored nucleotide barcode design unveils opportunities for large-scale sample multiplexing, Nucleic Acids Research, 2007, vol. 35, No. 19 e130.*
Kandpal et al., Selective enrichment of a large size genomic DNA fragment by affinity capture: an approach for genome mapping, Nucleic Acids Research, vol. 18, No. 7, 1990.*
Li et al., Cytochrome c and dATP-Dependent Formation of Apaf-1/Caspase-9 Complex Initiates an Apoptotic Protease Cascade, Cell, vol. 91,479-489, Nov. 14, 1997.*
Sanz et al., Cell-type-specific isolation of ribosome-associated mRNAfrom complex tissues, PNAS, Aug. 18, 2009, vol. 106, No. 33, 13939-13944.*
Gasiunas, et al., "Cas9-crRNA ribonucleoprotein complex mediates specific DNA cleavage for adaptive immunity in bacteria", PNAS, E2579-E2586, 2012.
Gnirke, et al., "Solution hybrid selection with ultra-long oligonucleotides for massively parallel targeted sequencing", Nature Biotechnology, 182-189, vol. 27, No. 2, 2009.
Jinek, et al., "RNA-programmed genome editing in human cells", eLife, 1-9, 2013.
Jinek, et al.,"A Programmable Dual-RNA-Guided DNA Endonuclease in Adaptive Bacterial Immunity", Science, 37 pages, 2012.
Lecong, et al., "Multiplex Genome Engineering Using CRISPR/Cas Systems", Science 339, 819-823, 2013.
Qi, et al., "Repurposing CRISPR as an RNA-Guided Platform for Sequence-Specific Control of Gene Expression", Cell, 152, 1173-1183, 2013.
Smolina, et al., "End invasion of peptide nucleic acids (PNAs) with mixed-base composition into linear DNA duplexes", Nucleic Acids Research, 2005, vol. 33, No. 17, 1-9.
Wu, et al., "Genome-wide binding of the CRISCRISCRISCRISPR endonuclease Cas9 in mammalian cells", Nature Biotechnology, 1-9, 2014.

(Continued)

*Primary Examiner* — Channing S Mahatan (57) ABSTRACT

A method of enriching for a fragment of a genome, as well as corresponding compositions and kits, are provided. In certain embodiments, the method comprises: (a) contacting a sample comprising fragmented DNA with a Cas9-gRNA complex comprising mutant Cas9 protein that has inactivated nuclease activity and a Cas9-associated guide RNA that is complementary to a site in the DNA, to produce a Cas9-fragment complex that comprises a fragment of the fragmented DNA; and (b) isolating the complex. In addition, other methods and compositions for Cas9/CRISPR-mediated nucleic acid manipulation are also provided.

20 Claims, 3 Drawing Sheets

(56) References Cited

OTHER PUBLICATIONS

Kaboord, Barbara et al., "Biotinylated DNA binding capacities of Pierce Avidin Supports," Thermo Scientific Pierce Protein Research Application Note # 14 AN0014.1, Apr. 2006, 2 pages.
Kraynack, Bryan A. et al., "Small Interfering RNAs Containing Full 2'-O-Methylribonucleotide-Modified Sense Strands Display Argonaute2/eIF2C2-Dependent Activity," RNA; vol. 12, No. 1, 2006, 163-176.
Schumacher, Jill M. et al., "Spnr, a Murine RNA-binding Protein That Is Localized to Cytoplasmic Microtubules," Journal of Cell Biology; vol. 129, No. 4, 1995, 1023-1032.
Uchil, Pradeep D. et al., "Nuclear Localization of Flavivirus RNA Synthesis in Infected Cells," Journal of Virology; vol. 80, No. 11, Jun. 2006, 5451-5464.

\* cited by examiner

NUCLEIC ACID ENRICHMENT USING CAS9

CROSS-REFERENCING

This application claims the benefit of U.S. provisional application Ser. No. 61/828,507, filed May 29, 2013 and 61/831,061 filed Jun. 4, 2013, which applications are incorporated by reference herein.

BACKGROUND

Methods for isolating fragments from a genome, i.e., the separation of selected regions of a genome from other regions, find use in a variety of genomic analysis applications, including, but not limited to SNP analysis, sequencing, mutation detection and the detection of chromosomal rearrangements.

SUMMARY

The present disclosure provides, inter alia, a method of enriching for a fragment of DNA. In certain embodiments, the method comprises: (a) contacting a sample comprising fragmented DNA with a Cas9-gRNA complex comprising mutant Cas9 protein that has inactivated nuclease activity and a Cas9-associated guide RNA that is complementary to a site in the DNA in the sample, to produce a Cas9-fragment complex that comprises a fragment of the fragmented DNA; and (b) isolating the Cas9-fragment complex. Compositions and kits for practicing the method are also provided. Other methods and compositions for Cas9/CRISPR-mediated nucleic acid manipulation are also provided

DEFINITIONS

The term "sample" as used herein relates to a material or mixture of materials, typically, although not necessarily, in liquid form, containing one or more analytes of interest. A sample may have a complexity of least $10^3$, at least $10^4$, at least $10^5$, $10^6$ or $10^7$ or more.

The term "nucleic acid sample," as used herein denotes a sample containing nucleic acids.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "target polynucleotide," as used herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51-60, 61 to 70, 71 to 80, 80 to 100, 100 to 150 or 150 to 200 nucleotides in length, for example.

The terms "double stranded" and "duplex" as used herein, describes two complementary polynucleotides that are base-paired, i.e., hybridized together.

The term "amplifying" as used herein refers to generating one or more copies of a target nucleic acid, using the target nucleic acid as a template.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "single nucleotide polymorphism," or "SNP" for short, refers to a single nucleotide position in a genomic sequence for which two or more alternative alleles are present at appreciable frequency (e.g., at least 1%) in a population.

The term "free in solution," as used here, describes a molecule, such as a polynucleotide, that is not bound or tethered to another molecule or to a solid surface.

The term "partitioning," with respect to a genome, refers to the separation of one part of the genome from the remainder of the genome to produce a product that is isolated from the remainder of the genome. Partitioning may be complete or partial. For example, one part of the genome may be completely separated from the remainder of the genome, or one part of the genome may be separated from only 50% of the genome, or the remainder of the genome may be depleted or reduced in concentration, relative to the selected part. The term "partitioning" encompasses enriching.

The term "genomic region," as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a cleaving site for a nicking endonuclease adjacent to a binding site for the oligonucleotide. The precise nucleotide sequence that flanks the oligonucleotide binding site in a test genome may be known or unknown.

The term "affinity tag," as used herein, refers to a moiety that can be used to separate a molecule to which the affinity tag is attached from other molecules that do not contain the affinity tag. In certain cases, an "affinity tag" may bind to the "capture agent," where the affinity tag specifically binds to the capture agent, thereby facilitating the separation of the molecule to which the affinity tag is attached from other molecules that do not contain the affinity tag. Examples of affinity tags include biotin, digoxygenin, peptide tags and protein tags (e.g., his-tags and the like).

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

The term "adaptor-ligated", as used herein, refers to a nucleic acid that has been ligated to an adaptor. The adaptor can be ligated to a 5' end and/or a 3' end of a nucleic acid molecule.

The term "adaptor" refers to a nucleic acid that is ligatable to one or both strands of a double-stranded DNA molecule. In some embodiments, an adaptor may be a hairpin adaptor. In another embodiment, an adaptor may itself be composed of two distinct oligonucleotide molecules that are base paired with one another. As would be apparent, a ligatable end of an adaptor may be designed to be compatible with overhangs made by cleavage by a restriction enzyme, or it may have blunt ends. Adaptors may comprise multiple sequence regions, such as restriction enzyme recognition sequences, molecular barcodes and/or primer binding sequences.

The term "genotyping," as used herein, refers to any type of analysis of a nucleic acid sequence, and includes sequencing, polymorphism (SNP) analysis, mutation analysis, analysis of copy number, (CNVs) and analysis to identify rearrangements or structural variants.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods such as those described by Oxford Nanopore Technologies or electronic-detection based methods such as Ion Torrent technology commercialized by Life Technologies.

The term "target sequence" refers to a sequence in a double-stranded DNA molecule, where the target sequence is bound, and, optionally cleaved or nicked by Cas9. In many cases, a target sequence may be unique in any one starting molecule and, as will be described in greater detail below, multiple different starting molecules (e.g., overlapping fragments) may contain the same target sequence. In some cases, the target sequence may be degenerate, that is, the target sequence may have base positions that may have variable bases. These positions may be denoted as Y, R, N, etc., where Y and R denote pyrimidine and purine bases, respectively, and N denotes any of the 4 bases.

The term "cleaving," as used herein, refers to a reaction that breaks the phosphodiester bonds between two adjacent nucleotides in both strands of a double-stranded DNA molecule, thereby resulting in a double-stranded break in the DNA molecule.

The term "nicking," as used herein, refers to a reaction that breaks the phosphodiester bond between two nucleotides in one strand of a double-stranded DNA molecule to produce a 3' hydroxyl group and a 5' phosphate group.

The terms "cleavage site," and "nick site," as used herein, refers to the site at which a double-stranded DNA molecule has been cleaved or nicked.

The terms "Cas9 enzyme" and "Cas9-gRNA complex" refer to a complex comprising a Cas9 protein and a guide RNA (gRNA). The guide RNA may be composed of two molecules, i.e., one RNA ("crRNA") which hybridizes to a target and provides sequence specificity, and one RNA, the "tracrRNA", which is capable of hybridizing to the crRNA. In another embodiment, the guide RNA may be a single molecule (i.e., a sgRNA) that contains crRNA and tracrRNA sequences. A Cas9 protein may be at least 60% identical (e.g., at least 70%, at least 80%, or 90% identical, at least 95% identical or at least 98% identical or at least 99% identical) to a wild type Cas9 protein, e.g., to the *Streptococcus pyogenes* Cas9 protein. The Cas9 protein may have all the functions of a wild type Cas 9 protein, or only one or some of the functions, including binding activity, nuclease activity, and nuclease activity.

For Cas9 to successfully bind to DNA, the target sequence in the genomic DNA should be complementary to the target-recognizing part of the gRNA sequence and must be immediately followed by the correct protospacer adjacent motif or "PAM" sequence. The PAM sequence is present in the DNA target sequence but not in the gRNA sequence. Any DNA sequence with the correct target sequence followed by the PAM sequence will be bound by Cas9. The PAM sequence varies by the species of the bacteria from which Cas9 was derived. The most widely used Type II CRISPR system is derived from *S. pyogenes* and the PAM sequence is NGG located on the immediate 3' end of the gRNA recognition sequence. The PAM sequences of Type II CRISPR systems from exemplary bacterial species include: *Streptococcus pyogenes* (NGG), *Neisseria meningitidis* (NNNNGATT), *Streptococcus thermophilus* (NNAGAA) and *Treponema denticola* (NAAAAC).

The term "Cas9-associated guide RNA" refers to a guide RNA as described above (comprising a crRNA molecule and a tracrRNA molecule, or comprising an RNA molecule that includes both crRNA and tracrRNA sequences). The Cas9-associated guide RNA may exist as isolated RNA, or as part of a Cas9-gRNA complex.

Reference to a Cas9-associated guide RNA is "complementary to" another sequence is not intended to mean that the entire guide RNA is complementary to the other sequence. A Cas9-associated guide RNA that is complementary to another sequence comprises a sequence that is complementary to the other sequence. Specifically, it is known that a Cas9 complex can specifically bind to a target sequence that has as few as 8 or 9 bases of complementarity with the guide Cas9-associated guide RNA in the complex. Off site binding can be decreased by increasing the length of complementarity, e.g., to 15 or 20 bases.

The term "Cas9 nickase" refers to a modified version of the Cas9 enzyme, as described above, containing a single inactive catalytic domain, i.e., either the RuvC- or the HNH-domain. With only one active nuclease domain, the Cas9 nickase cuts only one strand of the target DNA, creating a single-strand break or "nick". A Cas9 nickase is still able to bind DNA based on gRNA specificity, though nickases will only cut one of the DNA strands. The majority of CRISPR plasmids currently being used are derived from *S. pyogenes* and the RuvC domain can be inactivated by an amino acid substitution at position D10 (e.g., D10A) and the HNH domain can be inactivated by an by an amino acid substitution at position H840 (e.g., H840A), or at positions corresponding to those amino acids in other proteins. As is known, the D10 and H840 variants of Cas9 cleave a Cas9-induced bubble at specific sites on opposite strands of the DNA. Depending on which mutant is used, the guide RNA-hybridized strand or the non-hybridized strand may be cleaved.

The term "mutant Cas9 protein that has inactivated nuclease activity" refers to a Cas protein that has inactivated HNH and RuvC nucleases. Such a protein can bind to a target site in double-stranded DNA (where the target site is determined by the guide RNA), but the protein is unable to cleave or nick the double-stranded DNA.

As used herein and unless indicated to the contrary, the term "Cas9-gRNA complex" refers to a complex containing a Cas9 protein and a guide RNA.

As used herein and unless indicated to the contrary, the term "Cas9-fragment complex" refers to a complex containing a Cas9-gRNA and a DNA fragment to which the Cas9-gRNA complex binds.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The following references are explicitly incorporated by reference for their teachings on Cas9, gRNA, and other reagents that can be used herein: Gasiunas et al (Proc. Natl. Acad. Sci. 2012 109: E2579-E2586), Karvelis et al (Biochem. Soc. Trans. 2013 41:1401-6), Pattanayak et al (Nat. Biotechnol. 2013 31: 839-43), Jinek et al. (Elife 2013 2: e00471), Jiang et al (Nat. Biotechnol. 2013 31:233-9), Hwang et al (Nat. Biotechnol. 2013 31: 227-9), Mali et al (Science 2013 339:823-6), Cong et al (Science. 2013 339: 819-23), DiCarlo et al (Nucleic Acids Res. 2013 41: 4336-43) and Qi et al (Cell. 2013 152: 1173-83).

As would be appreciated, the method described below may be employed to enrich for sequences from many different types of nucleic acid sample, e.g., a cDNA sample or genomic sample. For example, the method described below could be readily modified to isolate particular cDNAs from total cDNA.

Method of Enriching for a Fragment of Genomic DNA

Figure 1:
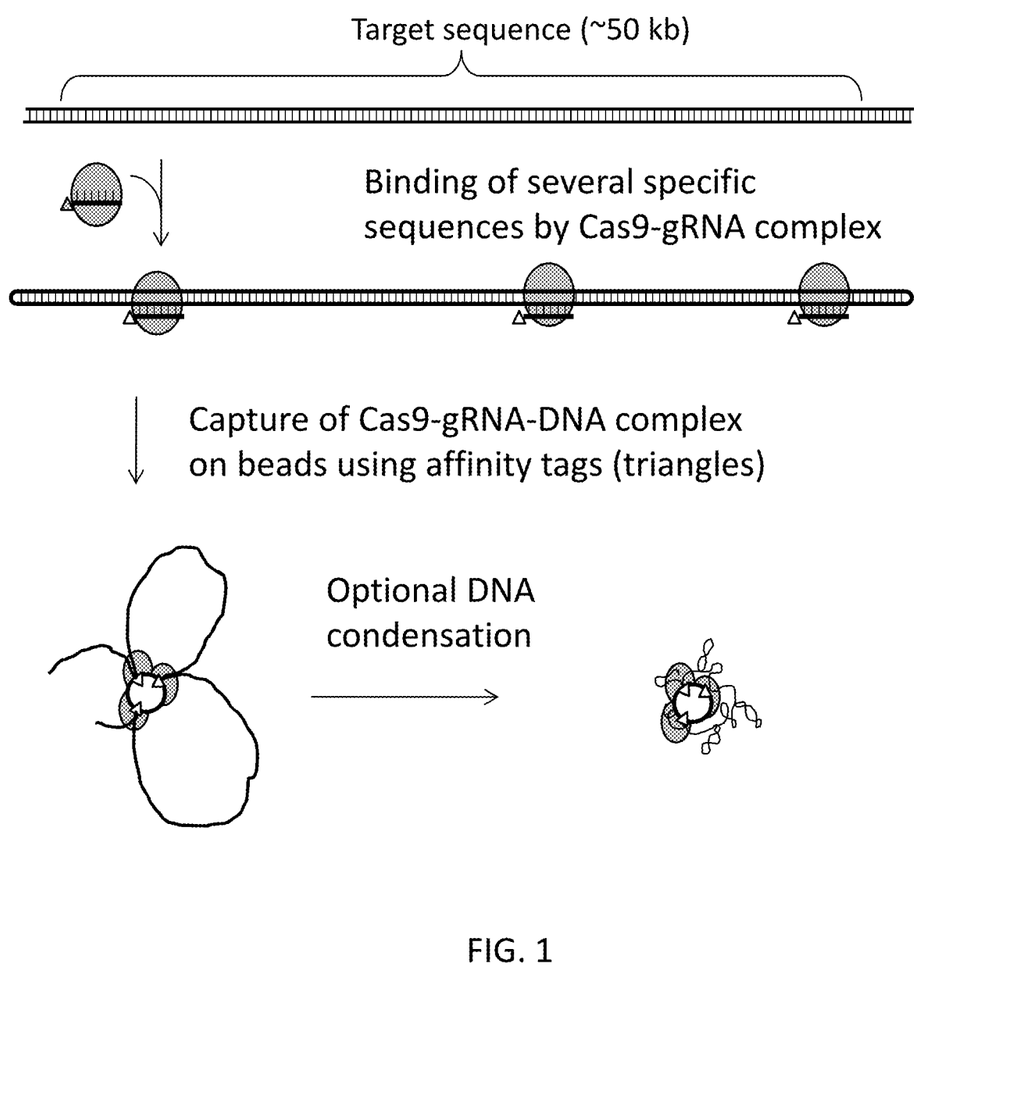
FIG. 1 schematically illustrates a method for capturing a single target using multiple capture probes.

As noted above, a method of enriching for a fragment of genomic DNA is provided. In certain embodiments, the method comprises: (a) contacting a sample comprising fragments of double-stranded genomic DNA with a Cas9-gRNA complex comprising a Cas9 protein, such as a mutant Cas9 protein that has an inactivated nuclease activity, and a Cas9-associated guide RNA that is complementary to a site in the DNA, to produce a complex that comprises a fragment of the fragmented genomic DNA; and (b) isolating the complex. In particular cases, a single Cas9 protein can be programmed with a library of guide RNAs, each targeting a different DNA site. By using a D10A H840A double mutant Cas9 protein, the protein will bind the DNA sequence targeted by the guide RNA, but will not cleave the DNA. The protein-target DNA complexes could then be collected by using an antibody against Cas9 or by using other means, e.g., an affinity tagged guide RNA or Cas9 protein, and genotyped. In particular cases, a single DNA sequence can be bound by several Cas9-gRNA complexes, which may enable the capture of longer target fragments, e.g., fragments over 10 kb or over 50 kb in length, as shown in FIG. 1. In some embodiments, a wild type Cas9 may be used, though it may have the additional effect of cleaving the target DNA sequence. However, if the Cas9 enzyme remains bound to the target DNA after cleavage, the target DNA may still be captured via Cas9 protein or the gRNA. In these embodiments, it may be beneficial to target both ends of a target region in the genome, such that cleavage by both Cas9 proteins will enable the capture of a precisely bounded region. Alternatively, a mixture of wild type and cleavage-deficient Cas9-gRNA complexes may be used, such that the wild type Cas9 proteins cleave the target segment from adjacent regions, and cleavage deficient Cas9 proteins are used to bind to one of more regions within the target segment, enabling efficient capture of the target segment.

As described above and in greater detail below, the method described herein may be used to isolated double-stranded DNA fragments from virtually any source, including but not limited to total genomic DNA and complementary DNA (cDNA), plasmid DNA, mitochondrial DNA, synthetic DNA, and BAC clones, etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the double-stranded DNA used in the method may be derived from a mammal, wherein certain embodiments the mammal is a human. In the description set forth above and below the method is used to isolate a fragment of genomic DNA. However, it is recognized that the same method can be used to isolate a fragment of double stranded DNA from another source.

In embodiments, in which genomic DNA is used, the genomic DNA may be isolated from any organism. The organism may be a prokaryote or a eukaryote. In certain cases, the organism may be a plant, e.g., *Arabidopsis* or maize, or an animal, including reptiles, mammals, birds, fish, and amphibians. In some cases, the test genome may be human or rodent, such as a mouse or a rat. Methods of preparing genomic DNA for analysis is routine and known in the art, such as those described by Ausubel, F. M. et al., (*Short protocols in molecular biology*, 3rd ed., 1995, John Wiley & Sons, Inc., New York) and Sambrook, J. et al. (*Molecular cloning: A laboratory manual*, $2^{nd}$ ed., 1989, Cold Spring Harbor Laboratory Press, Cold Spring Harbor, N.Y.). In certain cases, the sample used may contain total genomic DNA, which may be unamplified or amplified, e.g., genomic DNA that has been amplified by a whole genome amplification method, that may be undigested or digested with a restriction endonuclease (i.e., an enzyme that cleaves both strands to yield double-stranded fragments, where the restriction enzyme may have a four, five, six, seven, eight, nine, ten or greater than ten base pair recognition site) or fragmented by other means (see below).

The guide RNAs used in the method may be designed so that they direct binding of the Cas9-gRNA complexes to a genomic region of interest, e.g., a region under investigation such as a region of unknown sequence, or a region containing a SNP, nucleotide insertion, nucleotide deletion, rearrangement, etc. Since genomic isolation methods, and the nucleotide sequences of many organisms (including many bacteria, fungi, plants and animals, e.g., mammals such as human, primates, and rodents such as mouse and rat) are known, designing guide RNAs for use in the present method should be within the skill of one skilled in the art.

As noted above, in some embodiments the mutant Cas9 protein is inactivated in the sense that it can bind, but it cannot cleave, the sequence to which it has been programmed to bind by the gRNA complexed to it. In certain embodiments, the Cas9 protein has amino acid substitutions at D10 and H840, or sites corresponding thereto. In particular embodiments, the Cas9 protein may have D10A and H840A substitutions (or equivalent substitutions at positions corresponding to D10 and H840 in the *Streptococcus* Cas9 protein). Conditions for binding Cas9-rRNA complexes to target fragments are known and include, e.g., incubation in 10 mM Tris.HCl (pH 7.5), 10 mM NaCl, 0.1 mg/mL BSA, and 10 mM $MgCl_2$ at 37° C.

After the Cas9-gRNA complex has bound to the fragment, the isolating step of the method can be done in any convenient way. In some embodiments, the isolating is done using a capture agent (e.g., an antibody) that specifically binds to the Cas9 protein. In other embodiments, the Cas9 protein may itself be a fusion protein, where Cas9 protein is fused to a proteinaceous affinity tag such as avidin, streptavidin, protein A, maltose-binding protein, poly-histidine, HA-tag, c-myc tag, FLAG-tag, SNAP-tag, S-tag and glutathione-S-transferase (GST) or the like. Alternatively, the Cas9 protein can be conjugated to a non-proteinaceous affinity tag such as a biotin moiety (e.g., biotin). In these embodiments, the isolating can be done by binding the affinity tag to an affinity support, e.g., beads or the like, that contains a capture agent that specifically binds to the affinity tag. Similar methods for isolating duplex DNA fragments bound to peptide nucleic acids (PNAs) are described in Smolina et al (Nucleic Acids Res. 2005 Oct. 4; 33(17):e146) and are incorporated herein by reference.

In alternative embodiments, the Cas9-associated guide RNA may comprise an affinity tag, and the isolating may be done using a capture agent for the affinity tag. In these embodiments, the Cas9-associated guide RNA may comprises a biotin moiety, and the isolating may be done using an affinity support, e.g., beads or a column, that contains streptavidin or the like. Biotinylated RNA can be produced synthetically (e.g., using biotinylated ribonucleotides) or using any suitable enzymatic method (see, e.g., Moritz et al. *RNA* March 2014 20: 421-427). The affinity tag may be linked to the guide RNA at any position, including, but not limited to, the 5' end, the 3' end or any position in the interior of the oligonucleotide, e.g., in the middle of the oligonucleotide. In certain embodiments, the affinity tag may be cleavably linked to the guide RNAs such that the Cas9-fragment complexes can be cleaved from the support after the separation step. Methods for isolating target single stranded DNA with biotinylated RNA probes are known in the art, and similar methods have been published by Gnirke et al (*Nat. Biotechnol.* 2009 February; 27(2):182-9) and commercialized by Agilent Technologies as SureSelect Target Enrichment.

In some embodiments, a sample comprising fragmented DNA may be combined with a Cas9-gRNA complex that contains a mutant Cas9 protein that has inactivated nuclease activity and a Cas9-associated guide RNA that is complementary to a site in the DNA, and the resultant mixture may be combined with a support that contains a suitable binding agent e.g., beads or a column. The DNA fragments that are not bound by the Cas9-gRNA complex do not bind to the support and are washed through the column, whereas the fragments that are bound by the Cas9-gRNA complex are retained on the column. The Cas9-gRNA complexes (or the double-stranded DNA bound to the Cas9-gRNA complexes) can be released from the column by any suitable way. In general terms, the separating step may include contacting the Cas9-fragment complexes with a capture agent for the Cas9-gRNA complexes under conditions suitable for specific binding of the capture agent to the complex. Such conditions are known. The capture agent may be immobilized on a support, e.g., a bead, and, after the complexes are contacted with the capture agent, the resultant composition may be washed to remove unbound products from the solid support. The separation step thereby produces two fractions, one containing the selected genomic fragment (i.e., a fragment that is bound by the Cas9-gRNA complex) and the other that does not contain the selected region. In some embodiments, the fraction containing the bound fragment is used for further analysis, and the fraction that does not contain the selected region may be discarded. In other embodiments, the Cas9-gRNA is targeted towards undesired sequences (for example, highly repeated regions), and thus the fraction that contains the bound fragment is discarded, while the other fraction is used for further analysis.

In certain cases, the method may comprise contacting the fragmented genomic DNA with Cas9-gRNA complexes that contain a mutant Cas9 protein and a plurality of Cas9-associated guide RNAs that each comprise a sequence that is complementary to different sites in a defined region of the genomic DNA. In these embodiments, the defined region may be a contiguous sequence of nucleotides, which may be represented by one or more fragments in the sample (depending on how the fragmenting is done).

Cas9-gRNA complexes can be programmed to bind to any sequence, provided that the sequence has a PAM motif. In theory, the Cas9-gRNA complexes can bind to the fragment with an average interval in the range of 30-50 bp. However, in practice, the interval between the binding sites may be, e.g., in the range of 50-200 bp. In particular embodiments, the binding sites for the Cas9-gRNA complexes may be distributed along a defined region that may range in size from 1 kb to 500 kb, e.g., 5 kb to 100 kb.

As would be apparent, the method may be used to isolated several different fragments (i.e., at least 2, at least 5, at least 10, at least 50, at least 100 or at least 1,000 or more non-overlapping) fragments from the sample, where each fragment is bound by a plurality of different Cas9-gRNA complexes.

Depending on how the isolated fragment is going to be used, the sample containing fragments of genomic DNA may already be adaptor-ligated in that the molecules in the sample may contain an adaptor at one or both ends prior to being combined with the Cas9-gRNA complexes. In other embodiments, the isolated fragment may be ligated to an adaptor after it has been isolated.

The isolated fragment of double stranded DNA may be released from the isolated Cas9 complexes. This may be done by subjecting the isolated complexes to moderately denaturing conditions, thereby releasing the double-stranded DNA (in double-stranded form) from the Cas-9 complex, or in fully denaturing conditions (which may denature the strands of the isolated fragments) to yield single stranded DNA molecules. In other words, the selected genomic region may be isolated in single-stranded or double-stranded form. As such, in addition to the steps described above, the method may or may not further include denaturing the two strands of the selected fragment.

After the double stranded fragment is isolated, it may be genotyped. In particular embodiments, the double-stranded DNA may be sequenced. In certain embodiments, the fragment may be amplified using primers that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39) and Morozova et al (Genomics. 2008 92:255-64), which are incorporated by reference for the general descriptions of the methods and the particular steps of the methods, including all starting products, reagents, and final products for each of the steps.

In one embodiment, the isolated product may be sequenced using nanopore sequencing (e.g. as described in Soni et al. 2007 Clin Chem 53: 1996-2001, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology is disclosed in U.S. Pat. Nos. 5,795,782, 6,015,714, 6,627,067, 7,238,485 and 7,258,838 and U.S. Pat Appin Nos. 2006003171 and 20090029477.

The isolated fragments may be sequenced directly or, in some embodiments, the released fragments may be amplified (e.g., by PCR) to produce amplification products that are sequenced. In certain embodiments, isolated product may contain sequences that are compatible with use in, e.g., Illumina's reversible terminator method, Roche's pyrosequencing method (454), Life Technologies' sequencing by ligation (the SOLiD platform) or Life Technologies' Ion Torrent platform, as described above.

In certain embodiments, the sample may comprise a pool of fragmented genomic DNA from a plurality of samples, wherein the fragments in the sample have a molecular barcode to indicate their source. In some embodiments the double-stranded DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

Although the method may be effectively practiced on any double-stranded DNA fragment that is of any length, e.g., greater than 1 kb in length, the method finds particular utility when practiced on longer DNA molecules that are of, e.g., 5 kb to 200 kb, or longer. For example, the double-stranded DNA used in the method may a fragment of a genome that is in the range of 5 kb to 10 kb, 10 kb to 50 kb or 50 kb to 200 kb in length, or longer. Such fragments may be made by fragmenting a genome using physical methods (e.g., sonication, nebulization, or shearing), chemically, enzymatically (e.g., using a rare-cutting restriction enzyme, an engineered nuclease such as a ZFN, TALEN, or programmed Cas9-gRNA) or using a transposable element.

The method described above may be done using a single Cas9-gRNA complex or a plurality of Cas9-gRNA complexes that contain a Cas9 protein and a plurality (i.e., at least 2, at least 5, at least 10, at least 50, at least 100, at least 500 or at least 1,000, up to 10,000 or 100,000 or more) of Cas9 gRNAs in a multiplex reaction that can be used to isolate a plurality of different genomic regions. In certain embodiments, if a plurality of different Cas9-gRNA complexes are used, they may all contain the same affinity tag. In certain embodiments, if a plurality of different Cas9-gRNA complexes are used, several of the Cas9-gRNA complexes may bind to different sites in the same genomic region.

In particular cases, the efficiency of target DNA capture may also be enhanced by forming chemical crosslinks between the target DNA and the Cas9 protein. Alternatively, Cas9 could be programmed with a synthetic RNA that contains modified nucleotides or bases, such as nucleosides modified with thioethyl groups at the 2' position, or modified bases such as 4-thiouridine, 5-bromouridine, 5-iodouridine, and 6-thioguanosine. Modified synthetic RNAs could enable intra-strand crosslinking to the DNA target, allowing a chemical bond that would persist after denaturation or Cas9 protein removal.

Alternatively, the strands of the double-stranded molecules may be directly or indirectly linked by, e.g., ligating them to a hairpin adaptor, or clamping the top and bottom strands of a double-stranded DNA molecule to another using a protein (e.g., a thermostable clamping protein) that holds the strands of a double-stranded DNA molecule together under denaturing conditions. Using this method, the complementary strands are more able to "find each other" after denaturation, which greatly increases the efficiency of renaturation. Moreover, because the strands can be linked prior to denaturation, the complementary strands are paired in a way that reconstitutes the original double-stranded DNA molecule. The utility of such methods is discussed in, e.g., US20130323725, which is incorporated by reference.

In certain embodiments, inhibitors of DNases can be used to reduce degradation of DNA. DNase inhibitors that are compatible with Cas9 include, but are not limited to, 2-mercaptoethanol and actin.

Compositions

In addition to the method described above, a number of compositions are also provided. In certain embodiments, the composition may contain a Cas9-gRNA complex comprising a Cas9 protein which is able to cleave target DNA and a Cas9-associated guide RNA that is complementary to a site in genomic DNA. In certain embodiments, the composition may contain a Cas9-gRNA complex comprising a mutant Cas9 protein that has inactivated nuclease activity and a Cas9-associated guide RNA that comprise a sequence that is complementary to a site in genomic DNA. In certain embodiments, the composition may comprise a plurality of such guide RNAs, where each guide RNA in the population hybridizes to a different sequence in the genome. As would be apparent, the composition may contain a single Cas9 protein and a plurality of guide RNAs, e.g., at least 2, at least 10, at least 50, at least 100, at least 500, at least 1,000, at least 5,000 or at least 10,000 or more guide RNAs. The composition may also contain fragmented mammalian genomic DNA. In some cases, the Cas9 protein may contain an affinity tag, and other cases, the guide RNA(s) may contain an affinity tag. The guide RNAs may be at least 20, 30, 50, 75, 100, 150, 180, 200, 220, 240, or 260 nucleotides long. Such compositions may be employed in any embodiment disclosed herein.

The guide RNAs may be synthesized by enzymatic means, for example, by transcription by T7 RNA polymerase from DNA comprising a T7 promoter sequence. Alternatively, the guide RNAs may be synthesized on a solid support in an array, where the oligonucleotides are grown in situ. Oligonucleotide arrays can be fabricated using any means, including drop deposition from pulse jets or from fluid-filled tips, etc., or using photolithographic means. Polynucleotide precursor units (such as nucleotide monomers), in the case of in situ fabrication can be deposited. Oligonucleotides synthesized on a solid support may then be cleaved off to generate the population of oligonucleotides. Such methods are described in detail in, for example U.S. Pat. Nos. 7,385,050, 6,222,030, 6,323,043, and US Pat Appin Pub No. 2002/0058802, etc., the disclosures of which are incorporated herein by reference. The oligonucleotides may be tethered to a solid support via a cleavable linker, and cleaved from the support before use. In certain embodiments, the Cas9 protein is a mutant Cas9 that has amino acid substitutions that affects DNA binding, DNA cleavage, or gRNA binding.

Such compositions may be employed in any embodiment disclosed herein.

In certain embodiments, the Cas9 protein has amino acid substitutions at D10 and H840, or sites corresponding thereto.

In certain embodiments, the Cas9 protein is fused to an affinity tag.

In certain embodiments, the affinity tag is streptavidin.

In certain embodiments, the guide Cas9-associated guide RNA comprises an affinity tag, e.g., biotin.

In certain embodiments, the composition comprises guide Cas9-associated guide RNAs that comprise sequences complementary to sites are in a defined region, e.g., a defined region in the range of 1 kb to 200 kb.

In certain embodiments, the composition comprises guide Cas9-associated guide RNAs that comprise sequences complementary to sites that are distributed along a defined region.

In certain embodiments, the composition comprises a DNase inhibitor.

In certain embodiments the Cas9 protein has an amino acid sequence that at least 60% identical to a wild type Cas9 protein.

Kits

Also provided by the subject invention are kits for practicing the subject method, as described above. The subject kit contains mutant Cas9 protein that has inactivated nuclease activity and a set of at least 2, at least 5, at least 10, at least 15, at least 20, at least 30, at least 50, at least 75, at least 100, at least 200, at least 300, at least 400, at least 500, at least 600, at least 700, at least 800, at least 900, at least 1,000, or at least 10,000 or more guide RNAs, as described above. The Cas9 protein may contain an affinity tag, the guide RNAs may contain an affinity tag, or the kit may contain an antibody that binds to Cas9, for example. The guide RNAs may be in the form of a dried pellet or in an aqueous solution. The guide RNAs may be at least 20, at least 30, at least 50, at least 75, at least 100, at least 150, at least 180, at least 200, at least 220, at least 240, or at least 260 nucleotides long.

In addition to the instructions, the kits may also include one or more control genomes and or oligonucleotides for use in testing the kit. The subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kit as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The various components of the kit may be in separate containers, where the containers may be contained within a single housing, e.g., a box.

In certain embodiments, the Cas9 protein is a mutant Cas9 that has amino acid substitutions that affects DNA binding, DNA cleavage, or gRNA binding.

In certain embodiments, the Cas9 protein has amino acid substitutions at D10 and H840, or sites corresponding thereto.

In certain embodiments, the Cas9 protein is fused to an affinity tag.

In certain embodiments, the affinity tag is streptavidin.

In certain embodiments, the guide Cas9-associated guide RNA comprises an affinity tag, e.g., biotin.

In certain embodiments, the composition comprises guide Cas9-associated guide RNAs that comprise sequences complementary to sites are in a defined region, e.g., a defined region in the range of 1 kb to 200 kb.

In certain embodiments, the composition comprises guide Cas9-associated guide RNAs that comprise sequences complementary to sites that are distributed along a defined region.

In certain embodiments, the composition comprises a DNase inhibitor.

In certain embodiments the Cas9 protein has an amino acid sequence that at least 60% identical to a wild type Cas9 protein.

Utility

The above-described method may be used to partition a genome, i.e., to isolate one or more chosen regions of a genome (which may be single-stranded or double-stranded) from other regions of the genome. The genomic regions partitioned by the subject method may be arbitrarily chosen or, in some embodiments may have a common function, structure or expression. While the above-described method is not so limited, the method may be employed to isolate promoters, terminators, exons, introns, entire genes, homologous genes, sets of gene sequences that are linked by function, expression or sequence, regions containing insertion, deletion or translocation breakpoints or SNP-containing regions, for example. Alternatively, the method could be used to reduce the sequence complexity of a genome prior to analysis, or to enrich for genomic regions with fewer repeated sequences.

In certain embodiments the method may be used to enrich for one or more fragments (i.e., one or more regions of a genome), where the resultant sample is at least 50% free, e.g., at least 80% free, at least 90% free, at least 95% free, at least 99% free of the remainder of the genome, where at least 10%, at least 30%, at least 50%, at least 80% or at least 90% or at least 95% of the chosen genomic regions are partitioned into the isolated products and the remainder is partitioned into the unisolated products. As noted above, in addition to isolating a single genomic region, the method (when used with a plurality of different oligonucleotides in a multiplex reaction) can be used to enrich for a plurality of (i.e., at least 2, e.g., at least 5, at least 10, at least 50, at least 100, at least 500, at least 1,000, at least 5,000, at least 10,000 up to 50,000 or more) different genomic regions.

In particular embodiments, the products of the method may be amplified before analysis. In other embodiments, the products of the method may be analyzed in an unmodified form, i.e., without amplification.

As noted above, the method may be employed to isolate a region of interest from a genome. The isolated region may be analyzed by any analysis method including, but not limited to, DNA sequencing (using Sanger, pyrosequencing or the sequencing systems of Roche/454, Helicos, Illumina/Solexa, and ABI (SOLID)), a polymerase chain reaction assay, a hybridization assay, a hybridization assay employing a probe complementary to a mutation, a microarray assay, a bead array assay, a primer extension assay, an enzyme mismatch cleavage assay, a branched hybridization assay, a NASBA assay, a molecular beacon assay, a cycling probe assay, a ligase chain reaction assay, an invasive cleavage structure assay, an ARMS assay, or a sandwich hybridization assay, for example. Some products (e.g., single-stranded products) produced by the method may be sequenced and analyzed for the presence of SNPs or other differences relative to a reference sequence. As would be clear to one skilled in the art, the proposed method may be useful in several fields of genetic analysis, by allowing the artisan to focus his or her analysis on a genomic region of interest.

The subject method finds particular use in SNP haplotyping of a chromosomal region that contains two or more SNPs, for enriching for DNA sequences for paired-end sequencing methods, for generating target fragments for long-read sequences, isolating inversion, deletion, and translocation breakpoints, for sequencing entire gene regions (exons and introns) to uncover mutations causing aberrant splicing or regulation, and for the production of long probes for chromosome imaging, e.g., nanofluidic analysis, optical mapping, or fiber-FISH-based methods.

The method described above may also be used to study DNA methylation at the sequence level. Such methods are typically done by treating a target nucleic acid with sodium bisulfite. However, bisulfite modification can thwart hybridization-based approaches, because the modification changes the sequence of the unmethylated cytosines, creating an unknown number of mismatches with hybridization probes. Although the bisulfite sequence modification of constitutively methylated or unmethylated sequences can be predicted, these regions may be less relevant to biological research than partially methylated sequences (e.g., the "CpG shores"). Capture of longer DNA sequences allows the capture probes to bind sequences adjacent to the target region where the methylation level may be unknown or dynamically changing. A second issue with bisulfate modification of DNA is that the DNA is usually denatured during the treatment. Use of the method described above should address this issue, as the DNA could be renatured after the bisulfate treatment, and the resulting duplex DNA will be more stable for isolation and downstream analysis.

In particular cases, the method described above can also be used for long-range haplotyping by using hemizygous deletions to differentially label maternal and paternal chromosomes. Alternatively, heterozygous SNP could be targeted by the Cas9-gRNA, wherein the target sequence or the PAM sequence comprises the SNP site. The method may be employed to capture such hemizygous or heterozygous sequences together with adjoining sequence, and the capture should enrich or separate one allele (e.g., maternal) from the other allele (e.g., paternal.) In this way, maternal and paternal copies of DNA could be separated and analyzed independently. This would enable haplotype phased sequencing.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Alternative Embodiments

Also provided herein is a method for making vicinal nicks in genomic DNA. This method may comprise nicking vicinal sites in genomic DNA using a Cas9 nickase that is targeted to those sites; and replacing at least some of the sequence between the sites with a synthetic oligonucleotide. In this embodiment, Cas9 D10A or H840A mutants may be used because they are only capable of cleaving the top or bottom strands of the DNA target. These mutants could be used to create two single-stranded breaks on the same strand of DNA (vicinal nicks.) These vicinal nicks could be used to hybridize target oligonucleotides, enabling target enrichment.

For example, in one embodiment, the test genome may be nicked at two neighboring sites (i.e., "vicinal" sites) on the same strand that are 15 to 500 nucleotides (e.g., in the range of 18 to 200 nucleotides, in the range of greater than 25 to 200 nucleotides or in the range of greater than 50 to 200 nucleotides) apart, and the nicked region may be contacted with a molar excess (e.g., a 5- to 1.000-fold, e.g., 10- to 100-fold molar excess) of oligonucleotide under conditions suitable for strand displacement (i.e., displacement of the single-stranded nucleic acid between the nick sites by the oligonucleotide). Conditions for strand displacement are known (see, e.g., Walker, PCR Methods Appl. 1993 3:1-6; Kuhn et al. Nucleic Acids Res. 2008 36:e40; and Coma et al. Oligonucleotides 2005 15:269-83, among many others) and generally include non-stringent hybridization conditions (e.g., incubation, if a double-stranded target and an oligonucleotide, in a moderate temperature in the range of 30° C. to 70° C.). In certain embodiments of this method, the oligonucleotide may have a nucleotide sequence that is identical to the fragment that is being displaced. For example, if the fragment between the nick sites is 150 nucleotides in length, then the oligonucleotide may be 150 nucleotides in length. In other embodiments, the oligonucleotides may be longer or shorter than the replaced fragment by e.g., up to 5%, up to 10% or up to 20% or more, for example. Certain details of this method may be adapted from U.S. Pat. No. 8,017,328, which is incorporated by reference.

In certain embodiments this method may comprise:
(a) nicking vicinal sites in genomic DNA using a Cas9 nickase that is targeted to those sites; and
(b) replacing at least some of the sequence between the sites with a synthetic oligonucleotide.

In this embodiment, the Cas9 nickase may have an amino acid substitution at a position corresponding to D10 or H840.

In this embodiment, the Cas9 nickase may be a D10A or H840A mutant.

In this embodiment, the vicinal sites may be in the range of 15 to 500 nucleotides apart.

In this embodiment, the oligonucleotide may be in the range of 15 to 500 nucleotides in length.

In this embodiment, the replacing may be done by incubating the nicked genomic DNA with the synthetic oligonucleotide in non-stringent hybridization conditions.

In some embodiments, the non-stringent hybridization conditions include incubation at a temperature in the range of 30° C. to 70° C.

Also provided herein is a method for analyzing a genome. In this method, the method may comprise (a) contacting a genomic sample with one or more Cas9-gRNA complexes that cleave at sites that flank a locus that is polymorphic in length, to produce fragments; and (b) analyzing the length of the fragments. Short sequence repeats are highly polymorphic in humans, and thus can be used for identification purposes (often referred to as "DNA fingerprinting"). The Cas9/CRISPR system could be used to target repetitive elements in a target genome, or to cleave near the sites of fragment length polymorphisms, often associated with short DNA repeats. This cleaved DNA could be subjected to gel, Southern analysis (with or without PCR) or even sequencing for use in DNA fingerprinting to uniquely identify an individual.

In certain embodiments, the polymorphic locus may comprise a tandem repeat and in certain cases may contain microsatellite DNA. Microsatellites, also known as simple sequence repeats (SSRs) or short tandem repeats (STRs), are repeating sequences of 2-5 base pairs of DNA. One common example of a microsatellite is a (CA)n repeat, where n varies between alleles. These markers often present high levels of inter- and intra-specific polymorphism, particularly when the number of repetitions is 10 or greater. The repeated sequence is often simple, consisting of two, three or four nucleotides (di-, tri-, and tetranucleotide repeats respectively), and can be repeated 3 to 100 times, with the longer loci generally having more alleles due to the greater potential for slippage (see below). CA nucleotide repeats are very frequent in human and other genomes, and are present every few thousand base pairs. As there are often many alleles present at a microsatellite locus, genotypes within pedigrees are often fully informative, in that the progenitor of a particular allele can often be identified. In this way, microsatellites are ideal for determining paternity, population genetic studies and recombination mapping. It is also the only molecular marker to provide clues about which alleles are more closely related. Microsatellites are also predictors of SNP density as regions of thousands of nucleotides flanking microsatellites have an increased or decreased density of SNPs depending on the microsatellite sequence.

The following table lists some types of satellite repeats that can be analyzed using this method:

| Type | length of repeat | location |
|---|---|---|
| α (alphoid DNA) | 171 | All chromosomes |
| B | 68 | Centromeres of chromosomes 1, 9, 13, 14, 15, 21, 22 and Y |
| Satellite 1 | 25-48 | Centromeres and other regions in heterochromatin of most chromosomes |
| Satellite 2 | 5 | Most chromosomes |
| Satellite 3 | 5 | Most chromosomes |

The size of the bands analyzed may be in the range of 1-5 kb, although sizes outside of this range are envisioned. The analysis may be done by Southern blotting or by labeling fragments, separating the labeled fragments, and analyzing the sizes of the labeled fragments. In certain cases, the fragments may be amplified before analysis.

In certain embodiments, this method may comprise:
(a) contacting a genomic sample with one or more Cas9-gRNA complexes that cleave at sites that flank a locus that is polymorphic in length, to produce fragments; and
(b) analyzing the length of the fragments.

In some embodiments, this method may comprise cleaving a tandem repeat.

In some embodiments, this method may comprise cleaving microsatellite DNA.

In some embodiments, this method may comprise cleaving a short tandem repeat.

In some embodiments, the lengths of the fragments analyzed is in the range of 1 to 5 kb.

In some embodiments, the analyzing is done by labeling the fragments and separating them by size. s A method for processing a genome is also provided. This method may comprise: (a) contacting a genomic sample with one or more Cas9-gRNA complexes that cleave within a repetitive sequence, to produce: i. fragments of the repetitive sequence and ii. fragments comprising non-repetitive sequence; and (b) enriching for the fragments comprising non-repetitive sequence.

Figure 2:
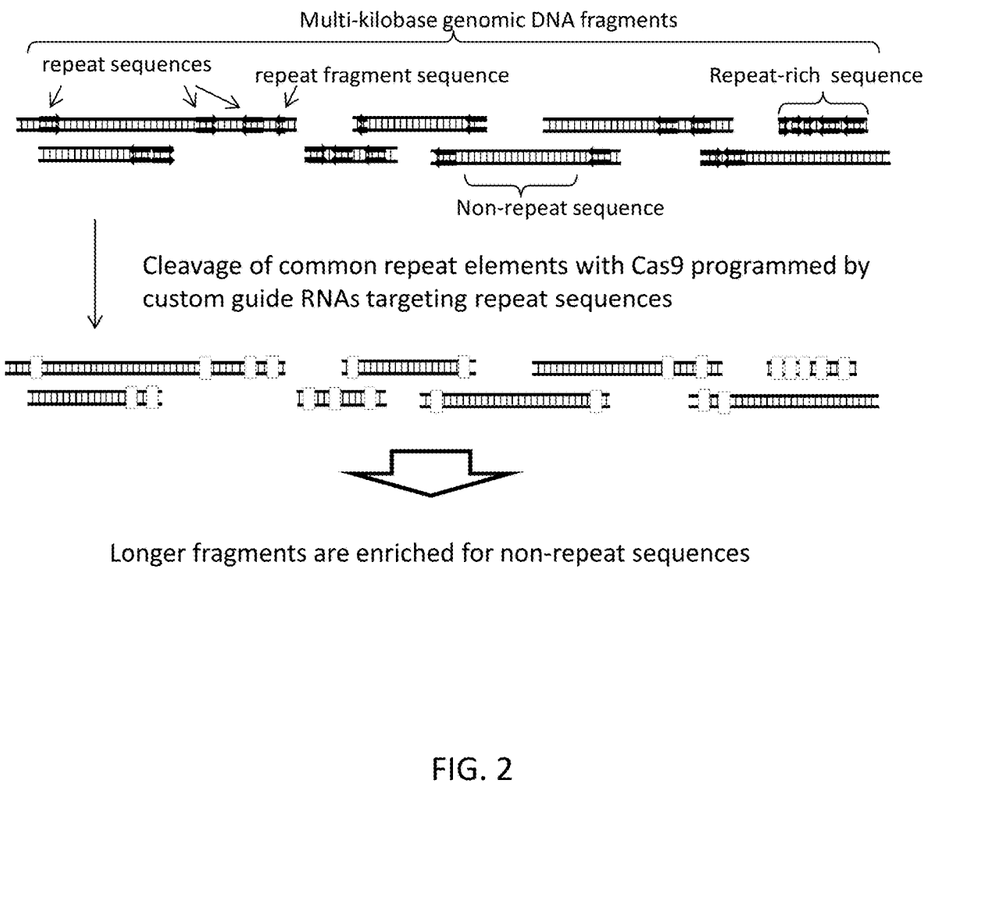
FIG. 2 schematically illustrates a method for targeting of repeat sequences with Cas9/CRISPR nucleases.
Figure 3:
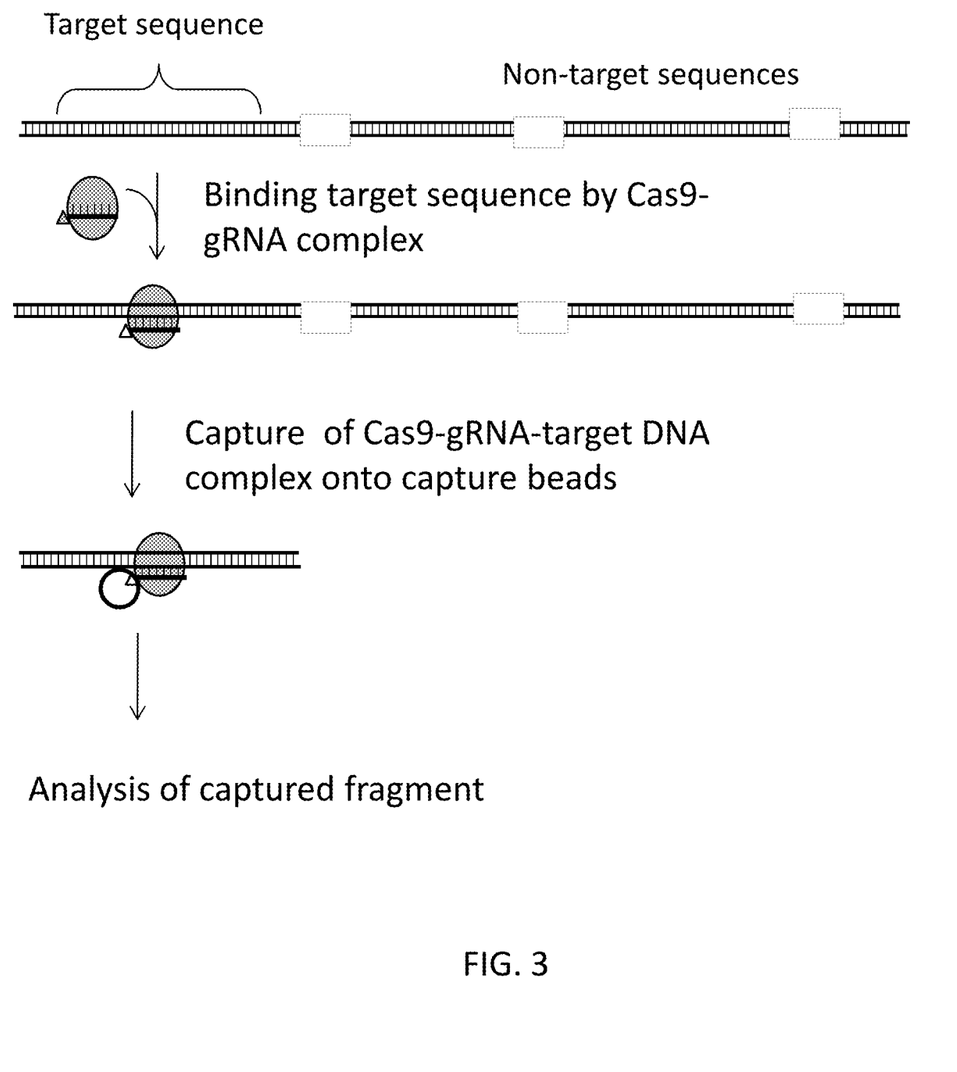
FIG. 3 schematically illustrates a method for capturing a single target using a single capture probe.

Some sequencing applications, such as whole genome sequencing for copy number estimation, require unbiased sequence representation of the entire genome. However, these methods are hindered by the repeat structure of the genome, since over half of the human genome is comprised of repeated sequences which do not map uniquely, and these are typically not useful for estimating copy number. This problem is worse in many plants, which have an even greater fraction of their genome made up by repeat elements. The Cas9/CRISPR system may offer one solution to this problem (FIG. 2). By programming the Cas9 protein with RNAs targeting repeat sequences, repeat elements could be selectively targeted and cleaved. Though this can already be done with restriction enzymes (note that the prevalent Alu sequence in the human genome is cleaved by the AluI restriction enzyme), the shorter recognition sequences of restriction enzymes will cause extensive fragmentation of non-repeat sequences. By targeting the most prevalent repeat elements with one or more guide RNAs, the repeat sequences could be fragmented, leaving the rest of the genomic sequence intact. As the recognition sequence for the Cas9/CRISPR system is 13-20 bp, even short fragments of repetitive elements could be targeted. A size selection step would substantially enrich the DNA for non-repeat-containing sequences. This "de-enrichment" approach may also be useful for long-read sequencing methods, as it may leave relatively intact large fragments. In certain embodiments, the non-repeat-containing sequences may be ligated to one another to form longer fragments which are depleted for repeat sequences.

In certain embodiments, the repeat sequences may be cleaved to any suitable size, e.g., to a size in the range of 13-200 bp and each repeat may be cleaved at multiple sites.

The smaller fragments (the repetitive sequences) may be separated from the larger fragments (containing the non-repetitive sequences) by any suitable method, including by size exclusion. In some embodiments, the repetitive sequences bound by the Cas9-gRNA complex may be separated from the fragments containing non-repetitive sequences by isolation of the Cas9-gRNA, together with the fragments containing repetitive sequences. In some embodiments, a Cas9 mutant or modified gRNA may be used, which may increase cleavage efficiency of the Cas9-gRNA complex. After separation, the longer fragments can be processed (e.g., cloned, amplified, sequenced, etc.).

This method may be used to effectively remove repetitive sequence from a sample, where the term "repetitive sequence" refers to a segment of DNA containing a sequence of nucleotides that is repeated for at least 5, 10, 15, 20, 30, 40, 50, 60, 80, or 100 or more times. Repetitive sequences can include single nucleotide repeats (homopolymer stretches, e.g., poly A or poly T tails), di-nucleotide repeats (e.g., ATAT or AGAG), tri-nucleotide repeats, tetra-nucleotide repeats, telomeric repetitive elements and the like. Repetitive sequences also include, but not limited to, ALU, LINE (long interspersed genetic elements, which are non-coding), SINE (short interspersed genetic elements, which also are non-coding), and certain transposons such as L and P element sequences. ALU elements are a type of SINE element, roughly 300 base pairs in length.

In certain embodiments, this method may comprise:
(a) contacting a genomic sample with one or more Cas9-gRNA complexes that cleave within a repetitive sequence, to produce: i. fragments of the repetitive sequence and ii. fragments comprising non-repetitive sequence; and
(b) enriching for the fragments comprising non-repetitive sequence.

In some embodiments, the repetitive sequence comprises sequence of nucleotides that is repeated in tandem for at least 5 times.

In some embodiments, the repeat sequences are cleaved to a size in the range of 13-200 bp.

In some embodiments, each repeat is cleaved at multiple sites.

In some embodiments, the repeat is a single nucleotide repeat, a di-nucleotide repeats, a tri-nucleotide repeats, a tetranucleotide repeat, or a telomeric repeat.

In some embodiments, the enriching is done by size exclusion.

Also provided herein is a method for removing adaptor dimers. In certain cases, this method comprises ligating adaptors to a fragment of nucleic acid to produce adaptor ligated fragments and adaptor dimers; and cleaving the adaptor dimers using a Cas9-gRNA complex, wherein the guide RNA of the Cas9-gRNA complex is specific for adaptor dimers. In this embodiment, the guide RNA may hybridize to the contiguous sequence produce by ligation of the adaptors to one another.

Several methods of library preparation for next-generation sequencing techniques involve ligation of primers or adapter sequences to target RNA or DNA. Several of these methods, such as Illumina's TruSeq method for RNA seq, can create dimers of the adapter sequences without an insert of target sequence, and these adapter dimers can consume a large fraction of the final sequence data without adding useful information. However, removal of adapter dimer sequences by restriction enzymes with short recognition sequences would also cleave a fraction of target inserts. Targeting adapter dimer sequences with a Cas9/CRISPR programmed nuclease could remove these sequences from the library without cleaving insert sequences.

In this embodiment, the adaptor dimer may contain two of the same adaptor molecule, or two different molecules, where the adaptors may be in the range of 6 to 100 bp or longer in length. The fragment of nucleic acid may be a fragment of genomic DNA or cDNA, and the source may a eukaryote, such as a mammal (e.g., human etc.), or a microbe.

After the adaptor dimers have been removed, the adaptor ligated fragments may be further processed and, e.g., sequenced.

Also provided herein is a method for removing aberrant assembly products. In this embodiment, the method comprises: a) performing an enzymatic reaction to assemble a synthon; b) contacting product of step a) with one or more Cas9-gRNA complexes that target and cleave predicted undesirable side-products that may be produced during assembly. In this embodiment, when multiple DNA fragments are assembled in synthetic biology, it is possible to get two fragments joined undesirably. Targeting all possible aberrant ligations with Cas9-gRNA complexes would cleave the undesired products, facilitating their removal.

The assembly may be done using any suitable method, including ligation and polymerase chain assembly, where the term "polymerase chain assembly", as used herein, refers to a protocol in which multiple overlapping oligonucleotides are combined and subjected to multiple rounds of primer extension (i.e., multiple successive cycles of primer extension, denaturation and renaturation in the presence of a polymerase and nucleotides) to extend the oligonucleotides using each other as a template, thereby producing a product molecule. In many cases, the final product molecule is amplified using primers that bind to sites at the ends of the product molecule, and the product molecule is digested with one or more restriction enzymes and cloned. Polymerase chain assembly may include additional steps, such as digestion of the product molecule with a restriction enzyme to, e.g., prepare the product molecule for cloning.

After the assembly has been completed and the aberrant products have been removed by treatment with Cas9, one or more synthons can be amplified by PCR and, e.g., cloned into an expression vector, for example.

In these embodiments, the method may comprise:
(a) ligating adaptors to a fragment of nucleic acid to produce adaptor ligated fragments and adaptor dimers; and
(b) cleaving the adaptor dimers using a Cas9-gRNA complex,
wherein the guide RNA of the Cas9-gRNA complex is specific for adaptor dimers.

In some embodiments, the guide RNA hybridizes to the contiguous sequence produced by ligation of the adaptors to one another.

In some embodiments, the fragments may be fragments of genomic DNA.

In some embodiments, the adaptor ligated fragments may be amplified by PCR after step (b).

In some embodiments, the adaptor ligated fragments may be sequenced after they are amplified.

Also provided herein is a method for making a recombinant plasmid. In certain embodiments, this method comprises: cleaving a target nucleic acid at specific sites using Cas9-gRNA complexes to produce a fragment; and cloning the fragment into a plasmid, thereby producing a recombinant plasmid. Even for moderately sized fragments of DNA (5 kb and above), it can be difficult to choose restriction enzymes which do not cleave the desired insert. The customizable 13-20 base pair specificity of a programmed Cas9/CRISPR system could be used to precisely cleave a targeted fragment from a larger DNA (e.g., cleave a gene or promoter sequence from genomic DNA) without cleaving the target fragment or vector in undesired places. In certain cases, one of the strands cleaved by the Cas9-gRNA complex is processed by a 3' to 5' exonuclease activity, leaving either a blunt end or a short 5' overhang, depending on the substrate and reaction conditions. However, these 3' recessed ends could be filled in with Taq polymerase, leaving a 3' terminal A residue that could enable TA-cloning.

In these embodiments, the fragment may have blunt ends and may be cloned into a blunt ended vector. In other embodiments, the fragment may be blunt-ended by filling-in using a polymerase, and then cloning the fragment into a vector. In particular cases, the polymerase used (e.g., Taq polymerase) may produce a 3' terminal A overhang, and the cloning may be done by TA cloning.

The length of the fragment may be in the range of 50 bp to 100 kb or more, e.g., 100 bp to 50 kb. In some cases, the length of the fragment may be 5 kb to 20 kb. Again, the target nucleic acid could be a fragment of any source, e.g., genomic DNA from a mammal or microbe.

In some embodiments, this method may comprise cleaving a target nucleic acid using a Cas9 enzyme to produce a fragment; treating the fragment with a 3' to 5' exonuclease to produce an overhang; filling in the overhang with one or more labeled nucleotides. The nucleotides may be, e.g., fluorescent or biotinylated, for example. A DNA polymerase could fill-in the ends with modified nucleotides such as biotinylated nucleotides, such that each Cas9-cleaved fragment has one or more 3' biotin moieties, enabling capture or fluorescent labeling of the Cas9-cleaved fragment. In these cases, it may be advantageous to first treat the DNA with ligase and/or terminal transferase and chain-terminator nucleotides, such that only the 3' ends of the DNA created by Cas9 cleavage could be labeled.

In these embodiments, the method may comprise:
(a) cleaving a target nucleic acid at specific sites using Cas9-gRNA complexes to produce a fragment; and
(b) cloning the fragment into a plasmid, thereby producing a recombinant plasmid.

In some embodiments, the fragment is in the range of 50 bp to 100 kb in length.

In some embodiments, the fragment is a fragment of genomic DNA.

In some embodiments the fragment is a fragment of a genome of a mammal or microbe In some embodiments, the method is done by TA cloning.

In some embodiments, the method comprises filling in an overhang in the fragment with one or more nucleotides.

In some embodiments, the method comprises filling in an overhang in the fragment with one or more labeled nucleotides.

Also provided herein is a method for labeling a site in a nucleic acid, comprising: (a) contacting the nucleic acid with a labeled complex comprising a mutant Cas9 protein that has inactivated nuclease activity and a guide RNA under conditions by which the complex binds to the nucleic acid; and (b) analyzing the product of step (a). Instead of capture and enrichment, custom target sequences could be fluorescently labeled using a labeled Cas9 protein, labeled chimeric guide RNA, or labeled antibody or streptavidin protein. Thus, duplex DNA sequences could be labeled at specific sites without the need for extensive denaturation, DNA polymerization, or digestion. Labeled DNAs could be examined by fluorescence microscopy (potentially coupled with microfluidic or nanofluidic analysis as described in Marie et al (J. Biophotonics. 2012 5:673-686) and Protozanova et al (Analytical Biochemistry 2010 402: 83-90). In certain embodiments, the nucleic acid may be an intact chromosome, e.g., a metaphase chromosome, and the nucleic acid may be in a cell or may be isolated. The analysis may be done by fluorescence microscopy or flow cytometry, methods for which are known. The labeled complex may be labeled using any convenient method. For example, the Cas9 protein may be fused to a fluorescent protein such as GFP or to streptavidin (which can be bound to a biotinylated fluorophore), or the guide RNA may be labeled with a fluorophore or with biotin (which can be bound by a fluorophore that is bound to streptavidin.) In general terms, the Cas9-guide RNA complexes may be bound to a sample containing intact chromosomes, and the binding is analyzed. For example, an interphase or metaphase chromosome preparation may be produced. The chromosomes are attached to a substrate, e.g., glass, contacted with the probe and incubated under suitable conditions. Wash steps remove all un-bound complexes, and the results are visualized and quantified using a microscope that is capable of exciting the dye and recording images.

Such imaging methods are generally known in the art and may be readily adapted for use herein. For example, the following references discuss in situ analysis methods: Ried et al., Human Molecular Genetics, 1998 7: 1619-1626; Speicher et al, Nature Genetics, 1996 12: 368-376; Schröck et al., Science, 1996 26:494-497; Griffin et al., Cytogenet Genome Res. 2007118(2-4):148-56; Peschka et al., Prenat Diagn., 199919(12):1143-9; Hilgenfeld et al, Curr Top Microbiol Immunol., 1999 246: 169-74. The chromosomes do not need to be denatured before being contacted with Cas9.

Fluorescence of a bound chromosome can be evaluated using, e.g., fluorescence microscopy. In general, excitation radiation, from an excitation source having a first wavelength, passes through excitation optics. The excitation optics causes the excitation radiation to excite the sample. In response, fluorescent molecules in the sample emit radiation that has a wavelength that is different from the excitation wavelength. Collection optics then collects the emission from the sample. A computer also can transform the data collected during the assay into another format for presentation. In general, known robotic systems and components can be used.

Certain fluorescent dyes may exhibit shifts of excitation or emission spectra depending on the local environment of the dye, or the environment may alter the probability of excitation or emission. Methods of using these environmentally sensitive dyes to detect binding to single stranded or double stranded nucleic acids are generally known in the art. In certain embodiments, environmentally sensitive fluorescent dyes may be used to detect binding of Cas9 or the gRNA to the DNA target, or detect conformation changes which may occur upon specific target site binding or cleavage. In embodiments, the environmentally sensitive dyes may be attached to the gRNA, or to Cas9 protein, or to the target DNA, or supplied as a component in the mixture of the Cas9-gRNA complex with the target DNA.

In certain embodiments, the signal from the binding of a labeled Cas9-gRNA complex to a chromosome may be compared with that of a reference chromosome. The reference chromosome may be from a healthy or wild-type organism. Briefly, the method comprises contacting a test chromosome from one cell with a plurality of labeled Cas9-gRNA complexes and contacting a reference chromosome with the same plurality of labeled Cas9-gRNA complexes. After binding, the emission spectra created from the unique binding patterns from the test chromosome are compared against those of the reference chromosome.

In these embodiments, the method may comprise:

(a) contacting the nucleic acid with a labeled complex comprising a mutant Cas9 protein that has inactivated nuclease activity and a guide RNA under conditions by which the complex binds to the nucleic acid; and (b) analyzing the product of step (a).

In certain embodiments, the product of step (a) is analyzed by fluorescence microscopy.

In certain embodiments, the product of step (a) is analyzed by FACS.

In certain embodiments, the Cas9 protein is fused to a fluorescent protein.

In certain embodiments, the guide RNA is labeled with a fluorophore.

In certain embodiments, the nucleic acid is an intact chromosome.

In certain embodiments, contacting is done in vivo.

In certain embodiments, contacting is done in vitro.

Any of the above-embodiments, may be done in a multiplex manner, i.e., using a plurality of different guide RNAs that target different sites in a nucleic acid.

What is claimed is:

1. A method comprising:
   (a) contacting a sample with a mutant Cas9 protein that has inactivated nuclease activity and a Cas9-associated guide RNA that has at least 15 complementary bases to a site in said genomic DNA genome followed by a protospacer adjacent motif, wherein the sample comprises fragmented genomic DNA, to produce a Cas9-fragment complex that comprises the mutant Cas9 protein and a fragment of the fragmented genomic DNA; and
   (b) isolating said Cas9-fragment complex.

2. The method of claim 1, wherein the Cas9 protein has amino acid substitutions at D10 and H840 in Cas9 derived from *S. pyogenes*, or sites corresponding to those amino acids in other proteins.

3. The method of claim 1, wherein said isolating is done using a capture agent that specifically binds to said Cas9 protein.

4. The method of claim 3, wherein said capture agent is an antibody.

5. The method of claim 1, wherein said Cas9-associated guide RNA comprises an affinity tag, and said isolating is done using a capture agent for said affinity, tag.

6. The method of claim 1, wherein the fragmented genomic DNA is made by fragmenting a genomic sample using Cas9.

7. The method of claim 1, wherein said Cas9 protein is a fusion with an affinity tag, and said isolating is done using a capture agent for the affinity tag.

8. The method of claim 1, further comprising: (c) releasing the fragment from the isolated Cas9-fragment complex of (b).

9. The method of claim 8, further comprising genotyping the released fragment.

10. The method of claim 9, wherein the genotyping is done by sequencing.

11. The method of claim 8, wherein the released fragment is a double-stranded fragment.

12. The method of claim 8, further comprising (d) amplifying the released fragments to produce PCR products.

13. The method of claim 12, further comprising sequencing the PCR products.

14. The method of claim 1, wherein the sample comprises a pool of fragmented genomic DNA from a plurality of samples, wherein the fragments in the sample have a molecular barcode to indicate their source.

15. A method comprising:
(a) contacting a sample comprising isolated fragmented genomic DNA with a mutant Cas9 protein that has inactivated nuclease activity and a Cas9-associated guide RNA that has at least 15 complementary bases to a site in said genomic DNA genome followed by a protospacer adjacent motif, wherein the sample comprises fragmented genomic DNA, to produce a Cas9-fragment complex that comprises the mutant Cas9 protein and a fragment of the fragmented genomic DNA, wherein the fragment is greater than 10 kb in length; and
(b) isolating said Cas9-fragment complex.

16. A method comprising:
(a) contacting a sample with a mutant Cas9 protein that has inactivated nuclease activity and a plurality of Cas9-associated guide RNAs that comprises guide RNAs having sequences complementary to different sites in the genomic DNA, where each Cas9-associated guide RNA has at least 15 complementary bases to one of the sites in said genomic DNA genome followed by a protospacer adjacent motif, wherein the sample comprises fragmented genomic DNA, to produce a Cas9-fragment complex that comprises the mutant Cas9 protein and a fragment of the fragmented genomic DNA; and
(b) isolating said Cas9-fragment complex.

17. The method of claim 16, wherein the different sites are in a defined region in the range of 1 kb to 200 kb.

18. The method of claim 17, wherein the defined region is one fragment larger than 10 kilobases.

19. The method of claim 16, wherein the different sites to which said Cas9-associated guide RNAs bind are distributed along a defined region.

20. The method of claim 16, wherein the different sites to which said Cas9-associated guide RNAs bind are distributed along a defined region in the range of 5 kb to 200 kb.

* * * * *